United States Patent [19]

Forster et al.

[11] 4,408,055
[45] Oct. 4, 1983

[54] AZOLYLOXY-CARBOXYLIC ACID N-OXY-AMIDE COMPOUNDS

[75] Inventors: Heinz Forster; Fritz Maurer; Volker Mues, all of Wuppertal; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 204,147

[22] Filed: Nov. 5, 1980

[30] Foreign Application Priority Data

Nov. 17, 1979 [DE] Fed. Rep. of Germany ....... 2946524

[51] Int. Cl.$^3$ ................. C07D 283/02; C07D 285/02; C07D 269/02; C07D 271/00
[52] U.S. Cl. .................................. 548/125; 548/129; 548/135; 548/132; 548/182; 548/209; 548/136; 548/144; 548/213; 548/221; 548/243; 71/88; 71/91; 71/92
[58] Field of Search ............... 548/187, 182, 125, 129, 548/132, 136, 144, 221, 229

[56] References Cited

U.S. PATENT DOCUMENTS 2,158,021  5/1939  Lichty .................................. 548/187
3,989,710  11/1976  Sasse et al. .......................... 548/187

FOREIGN PATENT DOCUMENTS 2914003  10/1980  Fed. Rep. of Germany ...... 548/182

*Primary Examiner*—Bernard Helfin
*Attorney, Agent, or Firm*—Felfe & Lynch

[57] ABSTRACT

Azolyloxy-carboxylic acid N-oxy-amide compound of the formula $$R-O-CH(R^1)-CO-N(OR^2)(R^3) \quad (I)$$

wherein

R is a five-membered hetero-aromatic monocyclic radical which contains an oxygen atom or a sulphur atom and in addition 1 to 3 nitrogen atoms and which is optionally substituted by halogen, cyano, nitro, amino, alkylamino, arylamino, dialkylamino, alkylcarbonylamino, alkylcarbonyl, carboxyl, alkoxycarbonyl, carbamoyl, alkylaminocarbonyl, dialkylaminocarbonyl, arylaminocarbonyl (which is optionally substituted by halogen, nitro or alkyl), aryl (which is optionally substituted by halogen, cyano, nitro, alkyl or alkoxy), by a radical which is optionally substituted by halogen and is selected from aralkyl, alkoxy, alkenoxy, alkynoxy, alkoxycarbonylalkoxy, aralkoxy, aryloxy, alkylthio, alkenylthio, alkoxycarbonylalkylthio, aralkylthio, arylthio, alkylsulphinyl, alkylsulphonyl, alkyl, alkenyl, alkynyl, alkoxyalkyl, aralkoxyalkyl, aryloxyalkyl, alkylthioalkyl, alkylsulphinylalkyl, alkylsulphonylalkyl, arylthioalkyl, arylsulphinylalkyl, arylsulphonylalkyl, carboxyalkyl, and alkoxycarbonylalkyl, or by optionally substituted aminocarbonylalkyl, cyanoalkyl or cycloalkyl, or which is optionally benzo-fused, the benzo radical optionally being substituted by halogen, alkyl, halogenoalkyl, alkoxy, halogenoalkoxy, alkylthio, halogenoalkylthio, amino, alkylamino, dialkylamino, nitro, cyano, alkoxycarbonyl or optionally halogen-substituted alkylenedioxy, $R^1$ is hydrogen or alkyl, and $R^2$ and $R^3$ are individually selected from optionally substituted radicals selected from the group consisting of alkyl, alkenyl, alkynyl, cycloalkyl, aralkyl, aryl or $R^2$ and $R^3$ taken together represent alkylene are effective herbicides.

23 Claims, No Drawings

AZOLYLOXY-CARBOXYLIC ACID N-OXY-AMIDE COMPOUNDS

This invention relates to certain new azolyloxy-carboxylic acid N-oxy-amide compounds, to herbicidal compositions containing them and to methods of combating undesired vegetation utilizing such compounds.

It has already been disclosed that certain phenoxycarboxylic acid amides, such as 2,4-dichlorophenoxy-acetamide, have a herbicidal action (see French Patent Specification No. 1,313,840). However, the phenoxycarboxylic acid amides known as herbicides have only a slight action against graminaceous weeds when applied in the customary amounts, and cannot be used for combating weeds in various dicotyledon cultures because of their deficient selectivity.

The present invention now provides, as new compounds, the azolyloxy-carboxylic acid N-oxy-amides of the general formula

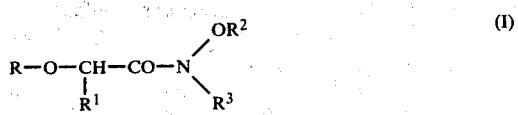
(I)

in which

R represents a five-membered hetero-aromatic monocyclic radical which contains an oxygen atom or a sulphur atom and in addition 1 to 3 nitrogen atoms and which is optionally substituted by halogen, cyano, nitro, amino, alkylamino, arylamino, dialkylamino, alkylcarbonylamino, alkylcarbonyl, carboxyl, alkoxycarbonyl, carbamoyl, alkylaminocarbonyl, dialkylaminocarbonyl, arylaminocarbonyl (which is optionally substituted by halogen, nitro or alkyl), aryl (which is optionally substituted by halogen, cyano, nitro, alkyl or alkoxy), by a radical which is optionally substituted by halogen and is selected from aralkyl, alkoxy, alkenoxy, alkynoxy, alkoxycarbonylalkoxy, aralkoxy, aryloxy, alkylthio, alkenylthio, alkynylthio, alkoxycarbonylalkylthio, aralkylthio, arylthio, alkylsulphinyl, alkylsulphonyl, alkyl, alkenyl, alkynyl, alkoxyalkyl, aralkoxyalkyl, aryloxyalkyl, alkylthioalkyl, alkylsulphinylalkyl, alkylsulphonylalkyl, arylthioalkyl, arylsulphinylalkyl, arylsulphonylalkyl, carboxyalkyl and alkoxycarbonylalkyl, or by optionally substituted aminocarbonylalkyl, cyanoalkyl or cycloalkyl, or which is optionally benzo-fused, the benzo radical optionally being substituted by halogen, alkyl, halogenoalkyl, alkoxy, halogenoalkoxy, alkylthio, halogenoalkylthio, amino, alkylamino, dialkylamino, nitro, cyano, alkoxycarbonyl or optionally halogen-substituted alkylenedioxy, and in which, R¹ represents a hydrogen atom or an alkyl radical and R² and R³, which are identical or different, represent an optionally substituted radical selected from alkyl, alkenyl, alkynyl, cycloalkyl, aralkyl and aryl, or together represent alkanediyl (alkylene).

According to the present invention there is further provided a process for the production of a compound of the present invention characterised in that an α-hydroxycarboxylic acid N-oxy-amide of the general formula

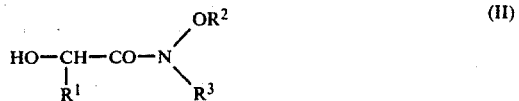
(II)

in which R¹, R² and R³ have the meaning indicated above, is reacted with a halogenoazole of the general formula

(III)

wherein

R has the meaning indicated above and

Hal represents a chlorine, bromine or iodine atom, optionally in the presence of an acid acceptor and optionally using a diluent.

The new azolyloxy-carboxylic acid N-oxy-amides of the present invention are distinguished by a powerful herbicidal activity.

Surprisingly, the new azolyloxy-carboxylic acid N-oxy-amides exhibit a considerably better herbicidal action than the phenoxycarboxylic acid amides known from the state of the art. It is particularly surprising that, coupled with good toleration by useful plants, the compounds according to the invention also exhibit a very good action against graminaceous weeds, in addition to their powerful action against dicotyledon weeds, whilst structurally similar phenoxyalkanecarboxylic acid derivatives, such as 2,4-dichlorophenoxy-acetamide, only exhibit a slight action against Graminaceae.

Preferred azolyloxy-carboxylic acid N-oxy-amides of the present invention are those of the general formula

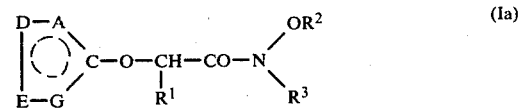
(Ia)

in which

A represents C-R⁴ or N,

D represents C-R⁵ or N,

E represents C-R⁶, N, O or S and

G represents C-R⁷, N, O or S, with the proviso that at least one of the ring members (A, D, E or G) represents N and at least one of the ring members represents O or S; and in which, R¹ represents a hydrogen atom or a methyl radical, R² represents an alkyl, alkoxyalkyl, alkenyl or alkynyl radical, in each case with up to 10 carbon atoms, and R³ represents an alkyl, alkoxyalkyl, alkenyl, alkynyl or cycloalkyl radical, in each case with up to 10 carbon atoms, an optionally halogen-substituted benzyl radical or a phenyl radical which is optionally substituted by C₁–C₄-alkyl, C₁–C₄-alkoxy, halogen, trifluoromethyl, cyano and/or nitro, and in which R⁴, R⁵, R⁶ and R⁷, which are identical or different independently represent a hydrogen or halogen atom or a nitro, cyano, amino, C₁–C₄-alkylamino, di-C₁–C₄-alkylamino, C₁–C₄-alkylcarbonylamino, C₁–C₄-alkyl-carbonyl, carboxyl, C₁–C₄-alkoxycarbonyl, carbamoyl, C₁–C₄-alkylamino-carbonyl or di-C₁–C₄-alkyl-amino-carbonyl radical, a phenylamino-carbonyl radical (which is optionally substituted by halogen, nitro or C₁–C₄-alkyl), a phenyl radical (which is optionally substituted by halogen, nitro, cyano, $C_1$–$C_4$-alkyl or $C_1$–$C_4$-alkoxy), an optionally halogen-substituted radical selected from benzyl, phenethyl, $C_1$–$C_4$-alkoxy, $C_2$–$C_4$-alkenoxy, $C_2$–$C_4$-alkynoxy, $C_1$–$C_4$-alkoxy-carbonylmethoxy, benzoyloxy, phenoxy, $C_1$–$C_4$-alkylthio, $C_2$–$C_4$-alkenylthio, $C_2$–$C_4$-alkynylthio, $C_1$–$C_4$-alkoxy-carbonyl-methylthio, benzylthio, phenylthio, $C_1$–$C_4$-alkyl-sulphinyl, $C_1$–$C_4$-alkylsulphonyl, $C_1$–$C_6$-alkyl, $C_2$–$C_6$-alkenyl and $C_2$–$C_6$-alkynyl or represents a cyano-$C_1$–$C_4$-alkyl, $C_1$–$C_4$-alkoxy-$C_1$–$C_2$-alkyl, phenoxy- or phenylthiomethyl, benzyloxy- or benzylthiomethyl, $C_1$–$C_4$-alkylthio-$C_1$–$C_2$-alkyl, $C_1$–$C_4$-alkyl- or phenylsulphinyl-$C_1$–$C_2$-alkyl, $C_1$–$C_4$-alkyl- or phenylsulphonyl-$C_1$–$C_2$-alkyl, carboxy-$C_1$–$C_2$-alkyl, $C_1$–$C_4$-alkoxy-carbonyl-$C_1$–$C_2$-alkyl, $C_1$–$C_4$-alkylaminocarbonyl-$C_1$–$C_2$-alkyl, di-$C_1$–$C_4$-alkylaminocarbonyl-$C_1$–$C_2$-alkyl, phenylaminocarbonyl-$C_1$–$C_2$-alkyl or $C_3$–$C_{12}$-cycloalkyl radical, or in which in each case two adjacent radicals $R^4$ and $R^5$, or $R^5$ and $R^6$, or $R^6$ and $R^7$ together represent a fused-on benzo radical which can be substituted by halogen, nitro, cyano or one or more optionally halogen-substituted radicals selected from $C_1$–$C_4$-alkyl, $C_1$–$C_4$-alkoxy, $C_1$–$C_4$-alkylthio and $C_1$–$C_2$-alkylenedioxy.

Particularly preferred compounds of the invention are those of the formula (I) in which $R^1$ represents a hydrogen atom, $R^2$ represents a $C_1$–$C_6$-alkyl, $C_1$–$C_4$-alkoxy-ethyl, allyl or propargyl radical and $R^3$ represents a $C_1$–$C_6$-alkyl, $C_1$–$C_4$-alkoxy-ethyl, allyl, propargyl, cyclopentyl, cyclohexyl or benzyl radical, and in which, R represents an azolyl radical selected from

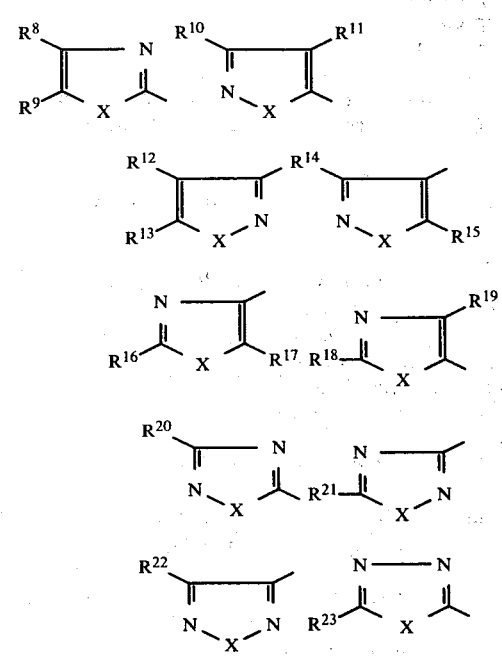

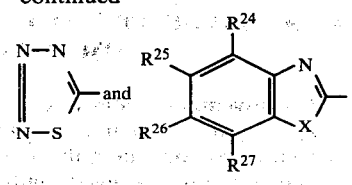

wherein

X represents oxygen or sulphur, the radicals $R^8$ to $R^{23}$, which can be identical or different, independently represent a hydrogen, bromine or chlorine atom or a nitro, cyano, $C_1$–$C_3$-alkylcarbonyl or $C_1$–$C_3$-alkoxycarbonyl radical, a phenyl radical which is optionally mono-substituted or disubstituted by fluorine, chlorine or bromine, methyl, methoxy, nitro, amino and/or cyano, or a phenoxy, phenylthio, $C_1$–$C_3$alkylthio, $C_1$–$C_3$-alkoxy, $C_1$–$C_3$-alkylsulphinyl, $C_1$–$C_3$alkylsulphonyl, $C_1$–$C_4$-alkyl, trifluoromethyl, cyano-$C_1$–$C_4$-alkyl, $C_2$–$C_4$-alkenyl, benzyloxymethyl, $C_1$–$C_3$-alkylamino, N-$C_1$–$C_3$-alkyl-N-$C_1$–$C_4$-alkyl-carbonylamino, phenoxymethyl-benzylthio or $C_1$–$C_3$-alkylcarbonyloxy radical, and the radicals $R^{24}$ or $R^{27}$, which can be identical or different, independently represent a chlorine atom, a $C_1$–$C_2$-alkyl, $C_1$–$C_2$-alkoxy, trifluoromethyl or trifluoromethoxy radical, or together represent methylenedioxy, dichloromethylenedioxy or difluoromethylenedioxy.

If, for example, 2,4,5-trichloro-thiazole and N-ethoxy-N-ethyl-hydroxyacetamide are used as starting substances, the course of the reaction for the preparation of compounds of the invention is illustrated by the following equation:

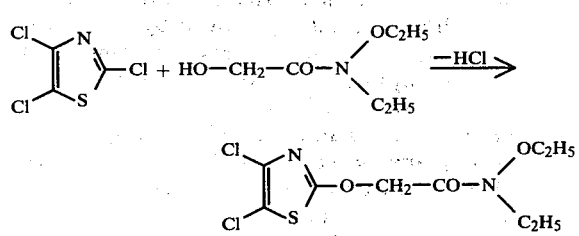

The process for the preparation of the new azoyloxycarboxylic acid amides is preferably carried out using suitable solvents or diluents. Possible solvents or diluents are virtually any of the inert organic solvents. These include, in particular, alcohols, such as methanol, ethanol, n- and iso-propanol and n-, iso-, sec.- and tert.-butanol, ethers such as diethyl ether, dibutyl ether, tetrahydrofurane and dioxane, ketones, such as acetone, methyl ethyl ketone, methyl isopropyl ketone and methyl isobutyl ketone, nitriles, such as acetonitrile and propionitrile, and the highly polar solvent dimethylformamide, dimethylsulphoxide, sulpholane and hexamethylphosphoric acid triamide.

Virtually any of the acid-bonding agents which can customarily be used can be employed as acid acceptors: these acid-binding agents include, in particular, alkali metal hydroxides or oxides and alkaline earth metal hydroxides or oxides, such as sodium hydroxide and potassium hydroxide and calcium oxide or calcium hydroxide, alkali metal carbonates and alkaline earth metal carbonates, such as sodium carbonate, potassium carbonate and calcium carbonate, alkali metal alcoholates, such as sodium methylate, ethylate and tert.butylate and potassium methylate, ethylate and tert.-butylate, and furthermore aliphatic, aromatic or heterocyclic amines, such as triethylamine, dimethylaniline, dimethylbenzylamine, pyridine, diazabicyclooctane and diazabicycloundecene.

The reaction temperature can be varied within a substantial range. In general, the reaction is carried out between $-50°$ and $+150°$ C., preferably at $-20°$ to $+100°$ C.

The process according to the invention is in general carried out under normal pressure.

In carrying out the process according to the invention, 1.0 to 1.5 moles of α-hydroxy-carboxylic acid amide of the formula (II) are employed per mole of halogenoazole of the formula (III). The reaction is in general carried out in a suitable diluent, and the reaction mixture is stirred at the required temperature for several hours.

The products are isolated by customary methods: some of the diluent is distilled off, if appropriate, under reduced pressure and the remainder of the reaction mixture is poured into water. If the products are thereby obtained as crystals, they are isolated by filtration. Otherwise, the organic products are extracted with a water-immiscible solvent, such as toluene or methylene chloride; after washing and drying, the solvent is then distilled off from the organic phase in vacuo. The products which remain are characterised by their melting point or their refractive index.

The α-hydroxy-carboxylic acid N-oxy-amides of formula (II) to be used as starting substances are novel compounds. Preferred compounds of formula (II) are those in which $R^1$, $R^2$ and $R^3$ represent those radicals which have already been mentioned in the definitions for preferred and particularly preferred compounds of the formula (I).

Examples of starting substances of the formula (II) which may be mentioned are: N-methoxy-N-methyl-, N-ethoxy-N-methyl-, N-n-propxy-N-methyl-, N-iso-propoxy-N-methyl-, N-ethoxy-N-ethyl, N-n-propoxy-N-ethyl, N-iso-propoxy-N-ethyl, N-n-propoxy-N-n-propyl-, N-iso-propoxy-N-isopropyl-, N-iso-propoxy-N-n-propyl-, N-methoxy-N-ethyl-, N-methoxy-N-n-propyl-, N-methoxy-N-isopropyl-, N-methoxy-N-n-butyl-, N-methoxy-N-isobutyl-, N-methoxy-N-sec.-butyl-, N-methoxy-N-sec.-hexyl-, N-ethoxy-N-n-propyl-, N-ethoxy-N-isopropyl-, N-(2-ethoxy-ethoxy)-N-methyl-, N-(2-ethoxy-ethoxy)-N-ethyl-, N-(2-ethoxy-ethoxy)-N-n-propyl-, N-(2-ethoxy-ethoxy)-N-isopropyl-, N-(2-ethoxy-ethoxy)-N-cyclohexyl-, N-allyloxy-N-allyl-, N-allyloxy-N-methyl-, N-allyloxy-N-ethyl-, N-allyloxy-N-n-propyl-, N-allyloxy-N-isopropyl-, N-allyloxy-N-n-butyl-, N-allyloxy-N-iso-butyl-, N-allyloxy-N-sec.-butyl, N-methoxy-N-cyclopentyl-, N-methoxy-N-cyclohexyl-, N-methoxy-N-(2-ethoxy-ethyl)-, N-ethoxy-N-(2-ethoxy-ethyl)-, N-(2-ethoxy-ethoxy)-N-(2-ethoxy-ethyl)- and N-(2-ethoxy-ethoxy)-N-sec.-hexyl-α-hydroxy-acetamide.

The new α-hydroxycarboxylic acid N-oxy-amides of the formula (II) can be prepared starting from α-chlorocarboxylic acid chloride of formula (IV), as illustrated in the equation below:

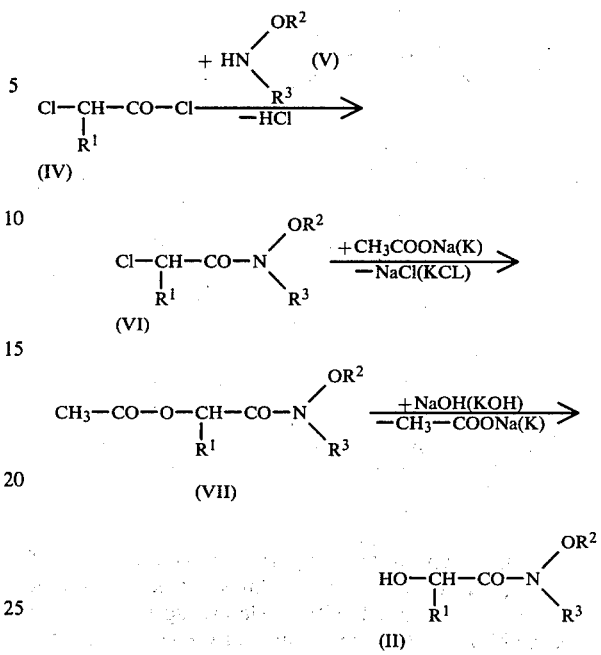

For this reaction, the α-chlorocarboxylic acid chlorides of the formula (IV), which are known from the literature, are first converted into the corresponding chlorocarboxylic acid N-oxy-amides of the formula (VI) with hydroxylamines of the formula (V), $R^1$, $R^2$ and $R^3$ having the meaning indicated above, if apporpriate in the presence of an acid-binding agent, such as triethylamine, and if appropriate using an inert diluent, such as 1,2-dichloroethane, at a temperature between $-20$ and $100°$ C., preferably between $-10°$ and $50°$ C. These products are worked up by customary methods, by washing with water, drying the organic phase and distilling off the solvent.

The compounds of the formula (VI) are reacted with sodium acetate or potassium acetate, if appropriate using a diluent, such as acetic acid or dimethylsulphoxide, at a temperature between 20° and 150° C., preferably between 50° and 120° C., to give the corresponding α-acetoxycarboxylic acid N-oxy-amides of the formula (VII). If the products are thereby obtained as crystals, they are isolated by filtration. Otherwise, working up is effected by customary methods, for example by distilling off the solvent in vacuo, taking up the residue in methylene chloride, washing the methylene chloride mixture with water and distilling off the solvent.

The compounds of the formula (VII) can be deacylated to give the compounds of the formula (II) by reaction with aqueous-alcoholic sodium hydroxide solution or potassium hydroxide solution at a temperature between 0° and 100° C., preferably between 10° and 50° C. To isolate the products, the solvents are distilled off in vacuo, the residue is extracted with an organic solvent, such as methylene chloride or ethyl acetate, the solution is dried and the solvent is distilled off.

The α-hydroxycarboxylic acid N-oxy-amides of formula (II) can also be prepared from the corresponding α-hydroxycarboxylic acids of formula (VIII), as illustrated in the following equation:

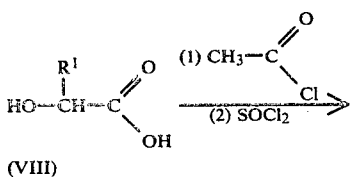

(VIII)

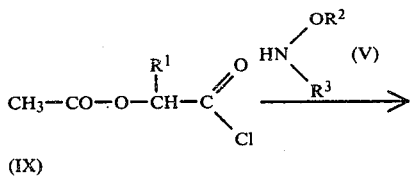

(IX)

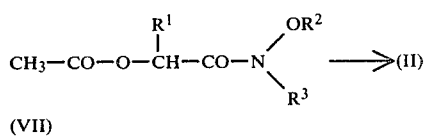

(VII)

For this reaction, the α-hydroxy-carboxylic acids of the formula (VIII), which are known from the literature, are first reacted with acylating agents, such as acetyl chloride, at a temperature between 0° and 50° C., preferably between 20° and 30° C., and the resulting reaction mixture are then treated with chlorinating agents, such as thionyl chloride, at a temperature between 20° and 100° C., preferably between 40° and 90° C.

The products of the formula (IX) thereby obtained, which are purified by distillation, can be converted into the α-acetoxycarboxylic acid N-oxy-amides of the formula (VII) in the conventional manner by reaction with the corresponding hydroxylamines of the formula (V), if appropriate in the presence of an inert diluent, and at a temperature between −10° and +50° C., preferably between 0° and +30° C. These products are deacylated as indicated above to give the compounds of the formula (II).

The intermediate products of the formulae (V), (VI) and (VII) in which at least one of the radicals $R^2$ and $R^3$ represents alkenyl, alkynyl, cycloalkyl or alkoxyalkyl are novel compounds. The preferred and particularly preferred meanings of $R^1$, $R^2$ and $R^3$ in these compounds are the same as those indicated above for the compounds of the formula (I).

The new hydroxylamines of the formula (V) are obtained by reacting N-alkoxycarbonyl-hydroxylamines of the general formula

(X)

in which
$R^2$ and $R^3$ have the meanings indicated above and
R′ represents a $C_1$–$C_4$-alkoxy radical, with aqueous-alcoholic alkali metal hydroxide solutions, such as with aqueous-ethanolic sodium hydroxide solution, at a temperature between 10° and 100° C.

For working up, the mixture is diluted with water and extracted with a water-immiscible organic solvent, such as, for example, methylene chloride; the extracts are dried, filtered and worked up by distillation.

The intermediate products (X) can be prepared by processes which are known from the literature (see for example, J. Amer. Chem. Soc. 66 (1944), page 1,931; see also the Preparative Examples).

Examples which may be mentioned of the new starting compounds of the formula (V), (X), (VI) and (VII) are: N-(2-ethoxy-ethoxy)-N-isopropyl-amine, -ethoxycarbonyl-amine, -chloroacetic acid amide and -acetoxyacetic acid amide; N-allyloxy-N-sec.-butylamine, -ethoxycarbonylmine, -chloroacetic acid amide and -acetoxyacetic acid amide; N-(2-ethoxy-ethoxy)-N-cyclohexyl-amine, -ethoxycarbonyl-amine, -chloroacetic acid amide and -acetoxyacetic acid amide; M-methoxy-N-cyclohexyl-amine, -ethoxycarbonylamine, -chloroacetic acid amide and -acetoxyacetic acid amide; N-(2-ethoxy-ethoxy)-N-methyl-amine, -ethoxycarbonylamine, -chloroacetic acid amide and acetoxyacetic acid amide; N-ethoxy-N-(2-ethoxy-ethyl)-amine, -ethoxycarbonylamine, -chloroacetic acid amide and -acetoxyacetic acid amide; N-(2-ethoxy-ethoxy)-N-(2-ethoxyethyl)-amine, -ethoxy-carbonylamine, -chloroacetic acid amide and -acetoxyacetic acid amide; N-methoxy-N-allyl-amine, -ethoxycarbonylamine, -chloroacetic acid amide and -acetoxyacetic acid amide; N-(2-ethoxy-ethoxy)-N-sec.-hexyl-amine, -ethoxycarbonyl-amine, -chloroacetic acid amide and -acetoxyacetic acid amide; and N-(2-ethoxy-ethoxy)-N-isopropyl-amine, -ethoxycarbonyl-amine, -chloroacetic acid amide and -acetoxyacetic acid amide.

Particularly preferred halogenazoles of formula (III) are those in which R has a meaning given in the definition of preferably or particularly preferred compounds of formula (I), and Hal represents a chlorine or bromine atom.

Examples of starting substances of the formula (III) which may be mentioned are: 2-chloro- and 2-bromo-oxazole and -thiazole, 2,4-dichloro-, 2,5-dichloro- and 2,4,5-trichloro-oxazole and -thiazole, 4-methyl-, 5-methyl-, 4-tert.-butyl-, 4,5-dimethyl-, 4-methyl-5-chloro-, 5-methyl-4-chloro-, 4-methyl-5-cyano-, 4-methyl-5-methoxycarbonyl-, 4-methyl-5-ethoxycarbonyl-, 4-methyl-5-isopropoxycarbonyl-, 4-methyl-5-acetyl-, 5-phenyl-, 4,5-diphenyl-, 4-chloro-5-phenyl-, 4-chloro-5-(3,4-dichloro-phenyl)- and 4-methyl-5-phenylthio-2-chlorooxazole, -2-bromo-oxazole, -2-chloro-thiazole and -2-bromo-thiazole; 3-tert.-butyl-4-cyano-, 3-but-3-en-1-yl-, 3,4-bis-ethoxycarbonyl-, 3-phenyl-, 3-ethyl-4-phenyl-5-chloro-isoxazole, 5-chloro-isothiazole, -5-bromo-isoxazole and -5-bromo-isothiazole; 3,5-bis-ethoxycarbonyl-4-chloro- and 3,5-bis-ethoxycarbonyl-4-bromo-isoxazole and -iso-thiazole; 3,5-dichloro-1,2,4-oxadiazole, 3-methyl-, 3-ethyl-, 3-n-propyl-, 3-iso-propyl-, 3-tert.-butyl-, 3-trifluoro-methyl-, 3-trichloromethyl-, 3-methylthio-, 3-methylsulphinyl-, 3-methylsulphonyl-5-chloro-1,2,4-thiadiazole and -5-bromo-1,2,4-thiadiazole; 4-methyl-, 4-ethyl-, 4-n-propyl- and 4-isopropyl-3-chloro-1,2,5-thiadiazole and -3-bromo-1,2,5-thiadiazole; 2-chloro- and 2-bromo-1,3,4-oxadiazole, 2-chloro- and 2-bromo-1,3,4-thiadiazole, 5-methyl-, 5-ethyl-, 5-n-propyl-, 5-iso-propyl-, 5-tert.-butyl-, 5-bromo-, 5-methylsulphinyl-, 5-ethylsulphinyl-, 5-propylsulphinyl-, 5-methylsulphonyl-, 5-ethylsulphonyl-, 5-propyl-sulphonyl-, 5-methoxycarbonyl-, 5-ethoxy-carbonyl-, 5-(1-cyano-2-methyl-propyl)-, 5-benzyloxymethyl-, 5-acetylamino-, 5-nitro-, 5-propylthio-, 5-trifluoromethyl-, 5-trichloromethyl-, 5-methylamino- and 5-(N-methyl-N-tert.-butylcarbonyl-amino)-2-chloro-1,3,4-oxadiazole, -2-bromo-1,3,4-oxadiazole, -2- chloro-1,3,4-thiadiazole and -2-bromo-1,3,4-thiadiazole; 2-chloro- and 2-bromobenzoxazole, 2-chloro- and 2-bromo-benzthiazole, 5-methyl-2-chloro-benzoxazole, 2-chloro-6-ethoxy-benzthiazole, 2,5-dichloro-benzoxazole, 2-chloro-6-trifluoromethyl-benzthiazole, 2-chloro-5-trifluoromethoxy-benzthiazole, 2-chloro-5,6-difluoromethylenedioxy-benzthiazole, 2,4,6,7-tetrachlorobenzthiazole, 2-chloro-4,6-difluoro-benzthiazole, 2-chloro-5-nitro-benzthiazole, 2-chloro-6-nitro-benzthiazole, 2-chloro-5-nitro-benzoxazole and 2-chloro-5-cyano-benzoxazole.

Halogenoazoles of the formula (III) are known (see Elderfield, Heterocyclic Compounds Volume 5 (1957), page 298 and page 452; Volume 7 (1961), page 463 and page 541; Weissberger, The Chemistry of Heterocyclic Compounds, (a) "Five-Membered Heterocyclic Compounds with Nitrogen and Sulfur or Nitrogen, Sulfur and Oxygen" (1952), page 35 and page 81, (b) "Five and Six-Membered Compounds with Nitrogen and Oxygen" (1962), page 5, page 245 and page 263; Advances in Heterocyclic Chemistry, Volume 5 (1965) page 119; Volume 7 (1966) page 183; Volume 17 (1974), page 99 and Volume 20 (1976), page 65; Synthesis 1978, 803; Tetrahedron Letters 1968, 829; Chem. Ber. 89 (1956), 1,534; 90 (1957), 182; 92 (1959), 1,928; J. Org. Chem. 27 (1962), 2,589; and DE-OS' (German Published Specifications) Nos. 1,670,706, 1,164,413 and 2,213,865).

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochroia, Fimbristylis, Sagittaria, Eleocharis, Scirpus, Paspalum, Ischaemum, Sphenoclea, Dactyloctenium, Agrostis, Alopercurus and Apera.

The active compounds according to the present invention may be used, for example, as selective herbicides in the following cultures:

dioctyledron cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

Besides a very good action against graminaceous weeds, the active compounds according to the invention also exhibit, in particular, a good herbicidal action against broad-leaved weeds. The active compounds according to the invention can be used selectively in various crops, for example in soya bean, cotton, maize, and beet.

The active compounds can be converted to the customary formulations, such as solutions, emulsions, wettable powders, suspensions, dusting agents, pastes, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaracides, nematicides, bird repellants, growth factors, plant nutrients and agents which improve soil structure, are also possible.

The active compounds can be used as such, in the form of their formulations or in the use forms prepare therefrom by further dilution, such as ready-to-use solutions, suspensions, emulsions, powders, pastes and granules. They are used in the customary manner, for example by watering, spraying, atomising, scattering or dusting.

The active compounds according to the invention can be applied either before or after emergence of the plants. They are preferably applied before emergence of the plants, that is to say by the pre-emergence method. They can also be incorporated into the soil before sowing.

The amount of active compound used can vary within a substantial range. It depends essentially on the nature of the desired effect. In general, the amounts used are between 0.01 and 10 kg of active compound per ha, preferably between 0.05 and 8 kg/ha.

The present invention also provides a herbicidal composition containing as active ingredient a compound of the present invention in admixture with a solid diluent or carrier or in admixture with a liquid diluent or carrier containing a surface-active agent.

The present invention further provides a method of combating weeds, characterised in that there is applied to the weeds, or to a habitat thereof, a compound of the present invention alone or in the form of a composition containing as active ingredient a compound of the present invention, in admixture with a diluent or carrier.

The present invention yet further provides crops characterised by being protected from damage by weeds by being grown in areas in which immediately prior to and/or during the time of growing a compound of the present invention was applied, alone or in admixture with a diluent or carrier.

The herbicidal activity of the compounds according to this invention is illustrated by the following biological test Example, in which the active compounds are each identified by the number (given in brackets) of the corresponding preparative Example given later in this specification.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparaton of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denoted:

0% = no action (like untreated control)
100% = total destruction

In this test, for example, the following compounds exhibited an excellent action: compounds (1), (2), (3), (5), (8), (10), (12), (13), (14), (15) and (16).

The following examples serve to illustrate the invention. The active compounds of the formula (I) according to the invention and the intermediate products of the formulae (II), (VI) and (VII) could in each case also be called hydroxamic acid derivatives.

PREPARATIVE EXAMPLES

Example 1

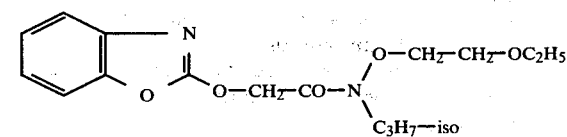

First 20.5 g (0.1 mole) of hydroxyacetic acid N-isopropyl-N-(2-ethoxyethoxy)-amide and then 15.4 g (0.1 mole) of 2-chlorobenzoxazole were added dropwise to a solution of 6.2 g (0.11 mole) of potassium hydroxide in 200 ml of isopropanol at 0° to 5° C., and the mixture was then subsequently stirred for 6 hours, without cooling. The solvent was then distilled off in vacuo, the residue was dissolved in 200 ml of toluene and the solution was extracted by shaking once with 100 ml of water. The organic phase was dried over sodium sulphate and evaporated in vacuo. The residue was subjected to incipient distillation at 60° C. under a high vacuum. 30.3 g (94% of theory) of benzoxazol-2-yl-oxyacetic acid N-isopropyl-N-(2-ethoxy-ethoxy)-amide were obtained in this manner in the form of a light brown oil with a refractive index $n_D^{22}$ of 1.4986.

The following compounds of the formula

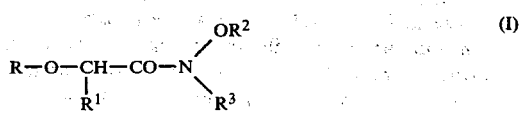

could be prepared in an analogous manner:

| Example No. | R | R¹ | R² | R³ | Physical data (Refractive index: melting point °C.) |
|---|---|---|---|---|---|
| 2 | 2-(4,5-dichlorothiazolyl) | H | $CH_3$ | $CH_3$ | 89 |
| 3 | 2-(4,5-dichlorothiazolyl) | H | $CH_2-CH_2-OC_2H_5$ | $C_3H_7$—iso | $n_D^{22}$: 1.5092 |
| 4 | 2-benzothiazolyl | H | $C_3H_7$—n | $C_3H_7$—n | 49 |
| 5 | 2-benzoxazolyl | H | $C_3H_7$—n | $C_3H_7$—n | 39 |
| 6 | 2-(4,5-dichlorothiazolyl) | H | $C_3H_7$—n | $C_3H_7$—n | $n_D^{21}$: 1.5131 |
| 7 | 2-(4,5-dichlorothiazolyl) | H | $C_3H_7$—iso | $C_3H_7$—iso | $n_D^{21}$: 1.5122 |
| 8 | 2-benzoxazolyl | H | $C_3H_7$—iso | $C_3H_7$—iso | 44 |
| 9 | 2-benzothiazolyl | H | $C_3H_7$—iso | $C_3H_7$—iso | $n_D^{21}$: 1.5491 |
| 10 | 2-benzoxazolyl | H | $CH_2-CH=CH_2$ | $CH_2-CH=CH_2$ | 49 |
| 11 | 2-benzothiazolyl | H | $CH_2-CH=CH_2$ | $C_4H_9$—sec. | $n_D^{22}$: 1.5582 |
| 12 | 2-(4,5-dichlorothiazolyl) | H | $CH_2-CH=CH_2$ | $C_4H_9$—sec. | $n_D^{22}$: 1.5167 |
| 13 | 2-benzoxazolyl | H | $CH_2-CH=CH_2$ | $C_4H_9$—sec. | $n_D^{22}$: 1.5219 |
| 14 | 2-benzoxazolyl | H | $CH_3$ | $C_4H_9$—sec. | 48 |

-continued
| Example No. | R | R¹ | R² | R³ | Physical data (Refractive index: melting point °C.) |
|---|---|---|---|---|---|
| 15 | 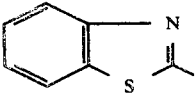 | H | CH₃ | C₄H₉—sec. | 52 |
| 16 | 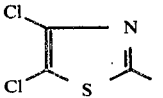 | H | CH₃ | C₄H₉—sec. | $n_D^{22}$: 1.5192 |
| 17 | 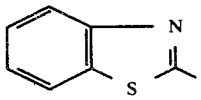 | H | CH₂—CH₂—OC₂H₅ | C₃H₇—iso | $n_D^{20}$: 1.5397 |
| 18 | 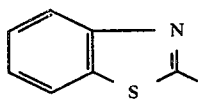 | H | CH₃ | 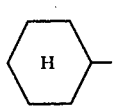 | 78 |
| 19 | 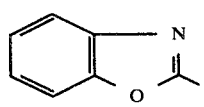 | H | CH₂—CH₂—OC₂H₅ | 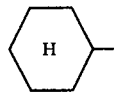 | $n_D^{25}$: 1.5138 |
| 20 | 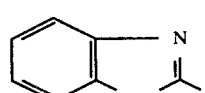 | H | CH₃ | 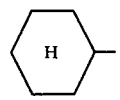 | 53 |
| 21 | 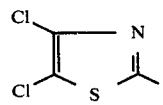 | H | CH₃ | 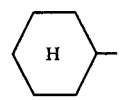 | 78 |
| 22 | 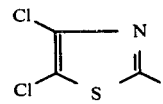 | H | CH₂—CH₂—OC₂H₅ | 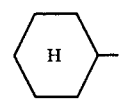 | $n_D^{22}$: 1.5231 |
| 23 | 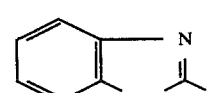 | H | CH₃ | CH₃ | 107 |
| 24 | 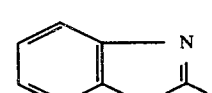 | H | CH₂—CH₂—OC₂H₅ | CH₃ | $n_D^{22}$: 1.5149 |
| 25 | 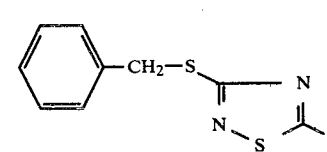 | H | CH₂—CH₂—OC₂H₅ | C₃H₇—iso | $n_D^{22}$: 1.4538 |
| 26 | 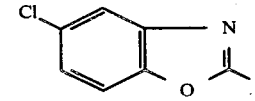 | H | CH₂—CH₂—OC₂H₅ | C₃H₇—iso | $n_D^{22}$: 1.5092 |

-continued

| Example No. | R | R$^1$ | R$^2$ | R$^3$ | Physical data (Refractive index: melting point °C.) |
|---|---|---|---|---|---|
| 27 | benzoxazol-2-yl | H | C$_2$H$_5$ | CH$_2$—CH$_2$—OC$_2$H$_5$ | n$_D^{22}$: 1.511 |
| 28 | benzoxazol-2-yl | H | CH$_2$—CH$_2$—OC$_2$H$_5$ | CH$_2$—CH$_2$—OC$_2$H$_5$ | n$_D^{21}$: 1.4988 |
| 29 | 3-methyl-1,2,4-thiadiazol-5-yl | H | CH$_2$—CH$_2$—OC$_2$H$_5$ | C$_3$H$_7$—iso | 40 |
| 30 | 3-methyl-1,2,4-thiadiazol-5-yl | H | CH$_3$ | C$_4$H$_9$—sec. | n$_D^{21}$: 1.4761 |
| 31 | 3-methyl-1,2,4-thiadiazol-5-yl | H | C$_3$H$_7$—iso | C$_3$H$_7$—iso | n$_D^{21}$: 1.4978 |
| 32 | 3-methylthio-1,2,4-thiadiazol-5-yl | H | CH$_2$—CH$_2$—OC$_2$H$_5$ | C$_3$H$_7$—iso | n$_D^{20}$: 1.5321 |
| 33 | 3-methylthio-1,2,4-thiadiazol-5-yl | H | C$_3$H$_7$—iso | C$_3$H$_7$—iso | n$_D^{20}$: 1.4705 |
| 34 | 3-methylthio-1,2,4-thiadiazol-5-yl | H | CH$_3$ | C$_4$H$_9$—sec. | n$_D^{20}$: 1.4895 |
| 35 | 3-chloro-1,2,4-oxadiazol-5-yl | H | CH$_3$ | C$_4$H$_9$—sec. | n$_D^{20}$: 1.4291 |
| 36 | 3-chloro-1,2,4-oxadiazol-5-yl | H | C$_3$H$_7$—iso | C$_3$H$_7$—iso | n$_D^{23}$: 1.4651 |
| 37 | 3-chloro-1,2,4-oxadiazol-5-yl | H | CH$_2$—CH$_2$—OC$_2$H$_5$ | C$_3$H$_7$—iso | n$_D^{22}$: 1.4981 |
| 38 | 3-methylsulfonyl-1,3,4-thiadiazol-2-yl | H | CH$_3$ | C$_4$H$_9$—sec. | 88° |
| 39 | 3-methylsulfonyl-1,3,4-thiadiazol-2-yl | H | CH$_2$—CH$_2$—OC$_2$H$_5$ | C$_3$H$_7$—iso | 57° |

-continued

| Example No. | R | R$^1$ | R$^2$ | R$^3$ | Physical data (Refractive index: melting point °C.) |
|---|---|---|---|---|---|
| 40 | C$_6$H$_5$–C(=N–N=C(CH$_3$))–S (1,3,4-thiadiazole with C$_6$H$_5$) | H | C$_3$H$_7$–iso | C$_3$H$_7$–iso | 102° |
| 41 | 5-Cl-benzoxazol-2-yl | H | C$_3$H$_7$–iso | C$_3$H$_7$–iso | 83° |
| 42 | 5-CH$_3$-benzoxazol-2-yl | H | CH$_3$–CH$_2$– | C$_3$H$_7$–iso | 51° |
| 43 | 5-Cl-benzoxazol-2-yl | H | CH$_3$ | C$_4$H$_9$–sec. | Fp: 71° |
| 44 | 4,5-dichloro-thiazol-2-yl | H | –CH$_2$–CH$_2$–OC$_2$H$_5$ | CH$_3$–CH(–C$_4$H$_9$–tert.) | $n_D^{20}$: 1.5062 |
| 45 | benzoxazol-2-yl | H | –CH$_2$–CH$_2$–OC$_2$H$_5$ | CH$_3$–CH(–C$_4$H$_9$–tert.) | $n_D^{20}$: 1.5040 |
| 46 | 3-iso-C$_3$H$_7$-1,2,4-thiadiazol-5-yl | H | C$_3$H$_7$–iso | C$_3$H$_7$–iso | $n_D^{25}$: 1.4861 |
| 47 | 3-iso-C$_3$H$_7$-1,2,4-thiadiazol-5-yl | H | CH$_2$–CH$_2$–OC$_2$H$_5$ | C$_3$H$_7$–iso | $n_D^{22}$: 1.4931 |
| 48 | 3-iso-C$_3$H$_7$-1,2,4-thiadiazol-5-yl | H | CH$_3$ | C$_4$H$_9$–sec. | $n_D^{20}$: 1.4896 |
| 49 | 3-n-C$_3$H$_7$-1,2,4-thiadiazol-5-yl | H | CH$_3$ | C$_4$H$_9$–sec. | $n_D^{22}$: 1.4368 |
| 50 | 3-n-C$_3$H$_7$-1,2,4-thiadiazol-5-yl | H | CH$_2$–CH$_2$–OC$_2$H$_5$ | C$_3$H$_7$–iso | $n_D^{22}$: 1.5033 |
| 51 | 3-n-C$_3$H$_7$-1,2,4-thiadiazol-5-yl | H | C$_3$H$_7$–iso | C$_3$H$_7$–iso | $n_D^{25}$: 1.4825 |
| 52 | 4-CH$_3$-5-CN-thiazol-2-yl | H | C$_3$H$_7$–iso | C$_3$H$_7$–iso | $n_D^{22}$: 1.5055 |

-continued

| Example No. | R | R¹ | R² | R³ | Physical data (Refractive index: melting point °C.) |
|---|---|---|---|---|---|
| 53 | 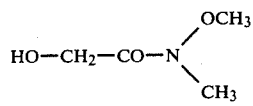 | H | $CH_2-CH_2-OC_2H_5$ | $C_3H_7$—iso | $n_D^{22}$: 1.5001 |
| 54 | 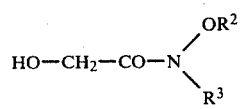 | H | $CH_3$ | $C_4H_9$—sec. | Fp: 55° |
| 55 | 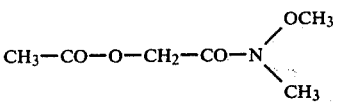 | | $CH_2-CH_2-OCH_3$ | $C_3H_7$—iso | Fp: 32° |

The hydroxycarboxylic acid N-oxy-amides to be employed as precursors could be prepared, for example, as follows:

EXAMPLE 56

$$HO-CH_2-CO-N\begin{matrix}OCH_3\\CH_3\end{matrix}$$

A mixture of 24.1 g (0.15 mole) of acetoxyacetic acid N-methyl-N-methoxy-amide, 100 ml of methanol and 0.2 g of potassium hydroxide powder was boiled under reflux for 2 hours. The solvent was then distilled off in vacuo. The residue was distilled in vacuo. 16.1 g (90% of theory) of hydroxyacetic acid N-methyl-N-methoxy-amide were obtained in this manner as a colourless liquid with a boiling point of 47° C. (0.1 mm Hg).

The following compounds of the formula $$HO-CH_2-CO-N\begin{matrix}OR^2\\R^3\end{matrix}$$

could be prepared in an analogous manner:

| Example No. | R² | R³ | Physical data (Refractive index: Boiling point °C.) |
|---|---|---|---|
| 57 | $CH_2-CH_2-OC_2H_5$ | $C_3H_7$-iso | $n_D^{24}$: 1.4485 |
| 58 | $C_3H_7$-n | $C_3H_7$-n | 77–80/0.1 |
| 59 | $C_3H_7$-iso | $C_3H_7$-iso | 63/0.1 |
| 60 | $CH_2-CH=CH_2$ | $CH_2-CH=CH_2$ | 76–78/0.1 |
| 61 | $CH_2-CH=CH_2$ | $C_4H_9$-sec. | 81/0.1 |
| 62 | $CH_3$ | $C_4H_9$-sec. | 64/0.1 |
| 63 | $CH_3$ | ⟨H⟩- | $n_D^{22}$: 1.4849 |
| 64 | $CH_2-CH_2-OC_2H_5$ | ⟨H⟩- | $n_D^{22}$: 1.4748 |
| 65 | $CH_2-CH_2-OC_2H_5$ | $CH_3$ | 90/0.1 |
| 66 | $CH_2-CH_2-OC_2H_5$ | $CH_2-CH_2-OC_2H_5$ | $n_D^{22}$: 1.4598 |

-continued

| Example No. | R² | R³ | Physical data (Refractive index: Boiling point °C.) |
|---|---|---|---|
| 67 | $CH_3$ | $\begin{matrix}CH_3\\CH\\C_4H_9\text{-tert.}\end{matrix}$ | |
| 68 | $CH_2-CH_2-OC_2H_5$ | $\begin{matrix}CH_3\\CH\\C_4H_9\text{-tert.}\end{matrix}$ | $n_D^{20}$: 1.4637 |
| 69 | $CH_2-CH_2-OCH_3$ | $C_3H_7$-iso | $n_D^{22}$: 1.4587 |
| 70 | $C_2H_5$ | $CH_2-CH_2-OC_2H_5$ | $n_D^{22}$: 1.4973 |

The acetoxy-carboxylic acid N-oxy-amides could also be prepared, for example, in the following manner:

EXAMPLE 71

$$CH_3-CO-O-CH_2-CO-N\begin{matrix}OCH_3\\CH_3\end{matrix}$$

A mixture of 23 g (0.28 mole) of sodium acetate, 200 ml of dimethylsulphoxide and 34.4 g (0.25 mole) of chloroacetic acid N-methyl-N-methoxy-amide (for its preparation, see DE-OS (German Published Specification) No. 2,753,182) was stirred at 70° C. for 7 hours. The mixture was then cooled to room temperature, 500 ml of methylene chloride were added and the inorganic salt was filtered off. The filtrate was evaporated in vacuo and the residue was distilled. 30.3 g (75% of theory) of acetoxyacetic acid N-methyl-N-methoxy-amide were thus obtained as a colourless liquid with a boiling point of 70° C./0.3 mm Hg.

EXAMPLE 72

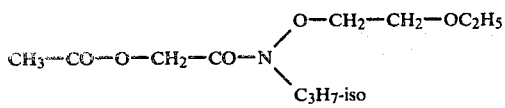

27.3 g (0.2 mole) of 2-acetoxyacetyl chloride were added to a mixture of 33.1 g (0.24 mole) of potassium carbonate, 200 ml of acetonitrile and 29.4 g (0.2 mole) of N-isopropyl-O-(2-ethoxyethyl)-hydroxylamine. During this addition, the temperature increased to about 30° C. The reaction mixture was subsequently stirred for a further 2 hours, without cooling, and was filtered and the solvent was distilled off in vacuo. 38 g (77% of theory) of acetoxy-acetic acid N-(2-ethoxyethoxy)-N-isopropyl-amide were thus obtained in the form of a colourless oil with a boiling point of 106°-107° C./0.1 mm Hg.

EXAMPLE 73

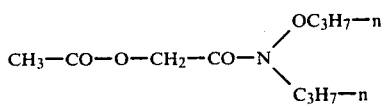

54.6 g (0.4 mole) of 2-acetoxyacetyl chloride were added dropwise to a mixture of 46.8 g (0.4 mole) of O,N-dipropylhydroxylamine, 250 ml of ethylene glycol dimethyl ether and 43.7 g (0.52 mole) of sodium bicarbonate at 10°-15° C. and the mixture was then subsequently stirred at room temperature for 2 hours. The salt which had separated out was then filtered off and rinsed with ethylene glycol dimethyl ether and the filtrate was than evaporated in vacuo. 80 g (92% of theory) of acetoxy-acetic acid N-n-propoxy-N-n-propyl-amide remained as a colourless liquid with a refractive index $n_D^{21}$ of 1.4438.

The following compounds of the formula

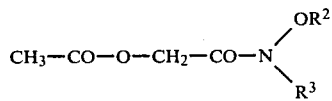

could be prepared analogously to one of the Examples 71 to 73.

| Example No. | $R^2$ | $R^3$ | Refractive index |
|---|---|---|---|
| 74 | $C_3H_7$—iso | $C_3H_7$iso | $n_D^{22}$: 1.4482 |
| 75 | $CH_2$—CH=$CH_2$ | $CH_2$—CH=$CH_2$ | $n_D^{23}$: 1.4642 |
| 76 | $CH_2$—CH=$CH_2$ | $C_4H_9$—sec. | $n_D^{21}$: 1.4573 |
| 77 | $CH_3$ | $C_4H_9$—sec. | $n_D^{21}$: 1.4428 |
| 78 | $CH_3$ |  | $n_D^{18}$: 1.4668 |
| 79 | $CH_2$—$CH_2$—$OC_2H_5$ |  | $n_D^{18}$: 1.4646 |
| 80 | $CH_2$—$CH_2$—$OC_2H_5$ | $CH_3$ | $n_D^{20}$: 1.4487 |
| 81 | $CH_2$—$CH_2$—$OC_2H_5$ | $CH_2$—$CH_2$—$OC_2H_5$ | $n_D^{20}$: 1.4385 |
| 82 | $CH_3$ | 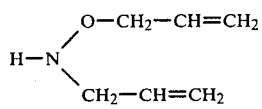 | $n_D^{22}$: 1.4233 |
| 83 | $CH_2$—$CH_2$—$OC_2H_5$ | (CH$_3$)CH—C$_4$H$_9$—tert. | $n_D^{20}$: 1.4405 |
| 84 | $CH_2$—$CH_2$—$OCH_3$ | $C_3H_7$—iso | $n_D^{20}$: 1.4221 |
| 85 | $C_2H_5$ | $CH_2$—$CH_2$—$OC_2H_5$ | $n_D^{20}$: 1.4831 |

The O,N-dialkylhdroxylamines, some of which are novel could be prepared, for example, as follows:

EXAMPLE 86

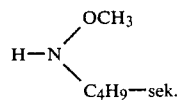

92.5 g (0.5 mole) of O,N-diallyl-N-carbethoxyhydroxylamine (for the preparation, see Kleinschmidt and Cope J. Amer. Chem. Soc. 66 (1944), page 1,931) were added to a mixture of 250 ml of water, 250 ml of ethanol and 150 ml of 45% strength sodium hydroxide solution. The solution was boiled under reflux for 3 hours, 300 ml of water were added and the mixture was extracted 3 times with 200 ml of methylene chloride each time. The combined organic phases were dried over sodium sulphate and the solvent was then distilled off. The residue was distilled in vacuo. 25 g (44% of theory) of O,N-diallylhydroxylamine were thus obtained as a colourless liquid with a boiling point of 33° C. (8 mm Hg).

EXAMPLE 87

H—N(OCH$_3$)(C$_4$H$_9$—sek.)

1st stage:
N-Phenyl-N'-sec.-butyl-N'-hydroxyurea

A mixture of 500 ml of ethylene glycol dimethyl ether, 209.1 g (1.5 moles) of 90% pure N-sec.-butylhydroxylamine hydrochloride and 151.2 g (1.8 moles) of sodium bicarbonate was stirred at room temperature for 1 hour and 178.5 g (1.5 moles) of phenyl isocyanate were then added at 0° to 5° C. The mixture was subsequently stirred at 10° C. for 1 hour, the salt was then filtered off and the filtrate was evaporated in vacuo. 310 g (99% of theory) of N-phenyl-N'-sec.-butyl-N'-hydroxyurea remained as a colourless powder with a melting point of 107° C.

2nd stage:
N-Phenyl-N'-sec.-butyl-N'-methoxyurea 164 g (1.3 moles) of dimethyl sulphate were added dropwise to a solution of 60 g (1.5 moles) of sodium hydroxide and 208 g (1 mole) of the abovementioned hydroxyurea in 500 ml of water at 30° C. The mixture was subsequently stirred at 25° to 30° C. for 2 hours and the product which had precipitated was then filtered off. 188 g (85% of theory) of N-phenyl-N'-sec.-butyl-N'-methoxy-urea were obtained in this manner in the form of colourless crystals with a melting point of 53° C.

3rd stage:
O-Methyl-N-sec.-butylhydroxylamine

A mixture of 241 g (2.6 moles) of aniline and 288.6 g (1.3 moles) of the methoxyurea described above was heated to 160° to 170° C. 83 g (62% of theory) of O-methyl-N-sec.-butylhydroxylamine were thereby distilled off as a colourless liquid of boiling point of 100° C./760 mm Hg.

The following compounds of the formula

could be prepared analogously to one of the Examples 86 and 87.

| Example No. | $R^2$ | $R^3$ | Boiling point (°C.(mm Hg) |
|---|---|---|---|
| 88 | $CH_2-CH_2-OC_2H_5$ | $C_3H_7$—iso | 57/10 |
| 89 | $CH_2-CH=CH_2$ | $C_4H_9$—sec. | 39/10 |
| 90 | $CH_2-CH_2-OC_2H_5$ | ⟨H⟩ | 63/0.1 |
| 91 | $CH_3$ | ⟨H⟩ | 63/13 |
| 92 | $CH_2-CH_2-OC_2H_5$ | $CH_3$ | 49/11 |
| 93 | $C_2H_5$ | $CH_2-CH_2-OC_2H_5$ | 59/10 |
| 94 | $CH_2-CH_2-OC_2H_5$ | $CH_2-CH_2-OC_2H_5$ | 97/10 |
| 95 | $CH_3$ | $CH(CH_3)(C_4H_9\text{—tert.})$ | 88/10 |
| 96 | $CH_2-CH_2-OC_2H_5$ | $CH(CH_3)(C_4H_9\text{—tert.})$ | 45/01 |
| 97 | $CH_2-CH_2-OCH_3$ | $C_3H_7$—iso | 99/10 |

It will be understood that the specification and examples are illustrative, but not limitative of the present invention and that other embodiments within the spirit and scope of the invention will suggest themselves to those skilled in the art.

What is claimed is:

1. Azolyloxy-carboxylic acid N-oxy-amide compound of the formula

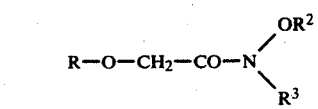

wherein $R^2$ represents a $C_1$-$C_6$-alkyl, $C_1$-$C_4$alkoxy-ethyl, allyl or propargyl radical and $R^3$ represents a $C_1$-$C_6$-alkyl, allyl, propargyl or cyclohexyl, and in which R represents an azolyl radical selected from

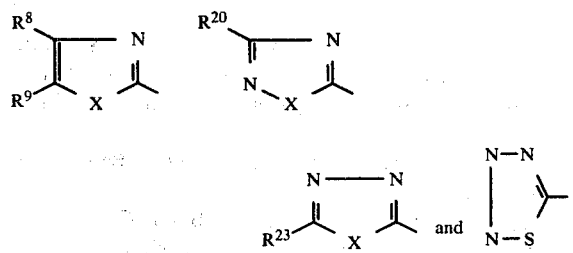

wherein

X represents oxygen or sulphur, the radicals $R^8$, $R^9$, $R^{20}$ and $R^{23}$ which can be identical or different, independently represent a hydrogen, bromine or chlorine atom or a nitro, cyano, $C_1$-$C_3$-alkyl-carbonyl or $C_1$-$C_3$-alkoxycarbonyl radical, a phenyl radical monosubstituted or disubstituted by fluorine, chlorine or bromine, methyl, methoxy, nitro, amino and/or cyano, or a phenoxy, phenylthio, $C_1$-$C_3$-alkylthio, $C_1$-$C_3$-alkoxy, $C_1$-$C_3$ alkylsulphinyl, $C_1$-$C_3$-alkylsulphonyl, $C_1$-$C_4$-alkyltrifluoromethyl, cyano-$C_1$-$C_4$-alkyl or $C_2$-$C_4$-alkenyl.

2. Azolyloxy-carboxylic acid N-oxy-amide compound as claimed in claim 1 designated 4,5-dichloro-thiazole-2-yl-oxyacetic acid N-isoporopyl-N-(2-ethoxyethoxy)-amide.

3. The compound of claim 1 wherein
$R_2$ and $R_3$ are independently selected from $C_1$-$C_6$ alkyl and
wherein
$R^8$, $R^9$, $R^{20}$ and $R^{23}$ are independently selected from hydrogen, bromine and chlorine.

4. The compound of claim 1 or 3 wherein
R is

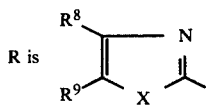

5. The compound of claim 1 or 3 wherein
R is

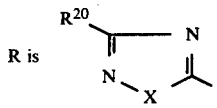

6. The compound of claim 1 or 3 wherein
R is

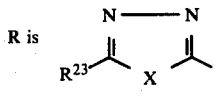

7. The compound of claim 1 or 3 wherein
R is

R is 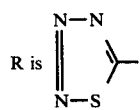

8. The compound of claim 1 wherein X is sulphur.
9. The compound of claim 1 wherein X is oxygen.
10. The compound of claim 1 wherein $R^2$ is $C_1$–$C_6$ alkyl.
11. The compound of claim 1 wherein $R^2$ us $C_1$–$C_4$ alkoxy-ethyl.
12. The compound of claim 1 wherein $R^2$ is allyl.
13. The compound of claim 1 wherein $R^2$ is propargyl.
14. The compound of claim 1 wherein $R^3$ is $C_1$–$C_6$-alkyl.
15. The compound of claim 1 wherein $R^3$ is allyl.
16. The compound of claim 1 wherein $R^3$ is propargyl.
17. The compound of claim 1 wherein $R^3$ is cyclohexyl.
18. The compound of claim 1 wherein $R^8$, $R^9$, $R^{20}$ and $R^{23}$ independently represent hydrogen, bromine or chlorine.
19. The compound of claim 1 wherein $R^8$, $R^9$, $R^{20}$ and $R^{23}$ independently represent nitro or cyano.
20. The compound of claim 1 wherein $R^8$, $R^9$, $R^{20}$ and $R^{23}$ independently represent $C_1$–$C_3$-alkylcarbonyl or $C_1$–$C_3$ alkoxycarbonyl.
21. The compound of claim 1 wherein $R^8$, $R^9$, $R^{20}$ and $R^{23}$ independently represent phenyl.
22. The compound of claim 1 wherein $R^8$, $R^9$, $R^{20}$ and $R^{23}$ independently represent mono or disubstituted phenyl.
23. The compound of claim 21 wherein said substituents are selected from fluorine, chlorine, and bromine.

* * * * *

UNITED STATES PATENT AND TRADEMARK OFFICE
CERTIFICATE OF CORRECTION

PATENT NO. : 4,408,055
DATED : October 4, 1983
INVENTOR(S) : Heinz Forster et al It is certified that error appears in the above-identified patent and that said Letters Patent is hereby corrected as shown below:

Claim 2, line 3, "isoporopyl" should be --isopropyl--.

Signed and Sealed this

Second Day of October 1984

[SEAL]

Attest:

Attesting Officer

GERALD J. MOSSINGHOFF

Commissioner of Patents and Trademarks